United States Patent
Hochrainer et al.

(10) Patent No.: US 7,247,496 B2
(45) Date of Patent: *Jul. 24, 2007

(54) PROCESS FOR DETERMINING THE PARTICLE SIZE DISTRIBUTION OF AN AEROSOL AND APPARATUS FOR CARRYING OUT SUCH A PROCESS

(75) Inventors: Dieter Hochrainer, Bingen am Rhein (DE); Georg Boeck, Mainz (DE); Hubert Hoelz, Oberheimbach (DE); Christian Scheffler, Ingelheim (DE); Christoph Kreher, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 460 days.

This patent is subject to a terminal disclaimer.

(21) Appl. No.: 10/202,572

(22) Filed: Jul. 24, 2002

(65) Prior Publication Data

US 2003/0054566 A1    Mar. 20, 2003

(30) Foreign Application Priority Data

Jul. 27, 2001    (DE) ............................. 101 36 555

(51) Int. Cl.
*G01N 31/00* (2006.01)
(52) U.S. Cl. ............... 436/174; 436/181; 436/164; 422/82.05; 422/83
(58) Field of Classification Search ......... 422/82.05, 422/83; 436/181, 164; 250/574; 356/336, 356/338
See application file for complete search history.

(56) References Cited

U.S. PATENT DOCUMENTS

| 3,809,478 | A | 5/1974 | Talbot |
| 5,250,186 | A | 10/1993 | Dollinger et al. |
| 5,957,124 | A | 9/1999 | Lloyd et al. |
| 6,315,984 | B1* | 11/2001 | Modi ........................ 424/45 |
| 6,386,015 | B1* | 5/2002 | Rader et al. ............... 73/31.05 |
| 2003/0034032 | A1* | 2/2003 | Ziegler et al. ......... 128/203.12 |

FOREIGN PATENT DOCUMENTS

| GB | 2340932 | 1/2000 |
| WO | WO 91/10123 | 7/1991 |

OTHER PUBLICATIONS

Stein, Stephen W.; Size distribution measurements of metered dose inhalers using Andersen Mark II cascade impactors, International Journal of Pharmaceutics, p.D. 199, p. 43-52—XP-002224771.

(Continued)

*Primary Examiner*—Jill Warden
*Assistant Examiner*—Samuel Siefke
(74) *Attorney, Agent, or Firm*—Michael Morris; Mary-Ellen M. Devlin; Thomas Blankinship

(57) ABSTRACT

The measurement of the particle size distribution of an aerosol is of crucial importance in pharmaceutical development. A prerequisite for this is a valid method, e.g. the cascade impactor method described in the pharmacopoeias. It requires measurement of the active substance concentration in order to determine the particle size distribution. The invention provides a process which makes it possible to measure the size of aerosol droplets containing pharmaceutical substances which are unstable in the event of changes in the pH.

11 Claims, 7 Drawing Sheets

OTHER PUBLICATIONS

Kippax, P., et al; Analysis of dry powders aerosols using laser diffraction British Pharmaceutical Conference 2001 Abstract Book, 121—XP002224772.

M. Dolovich, Measurement of Particle Size characteristics of Metered Dose Inhaler (MDI) Aerosols, Journal of Aerosol Medicine, Jul. 1991, pp. 251-263, 4(3).

* cited by examiner

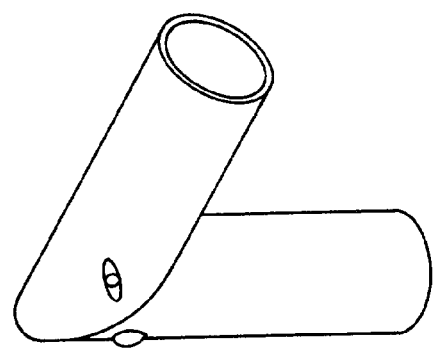
Fig.2d
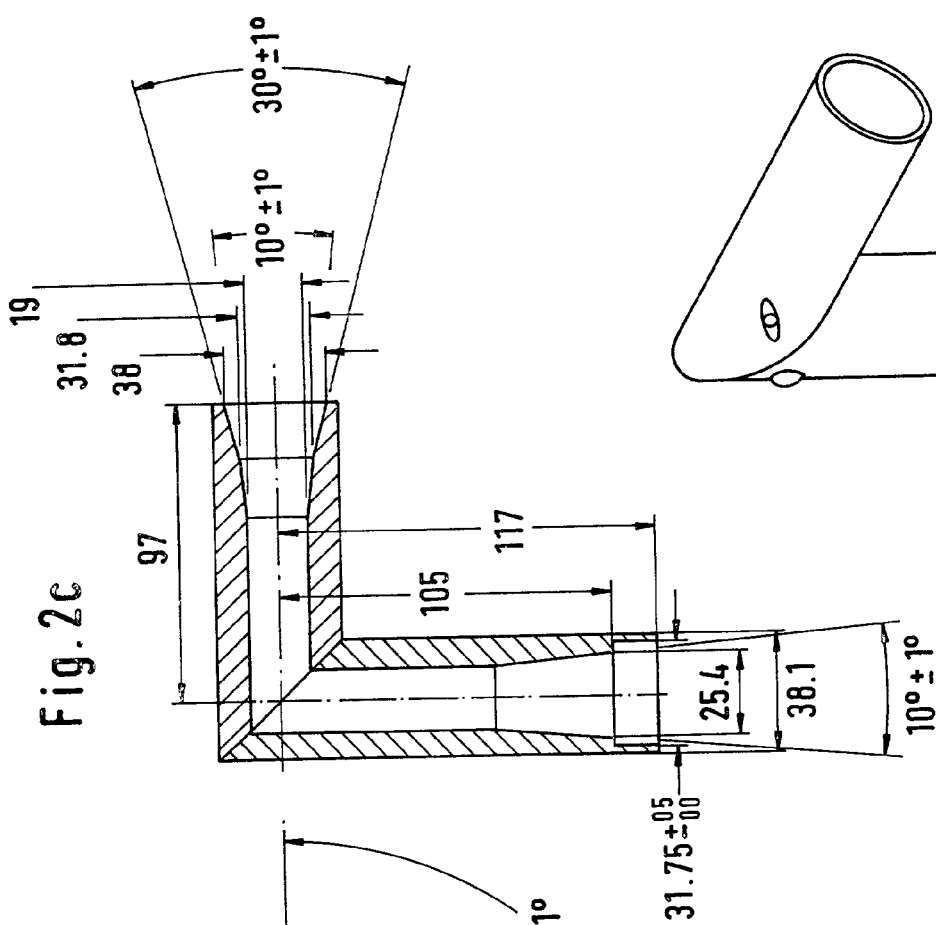
Fig.2c
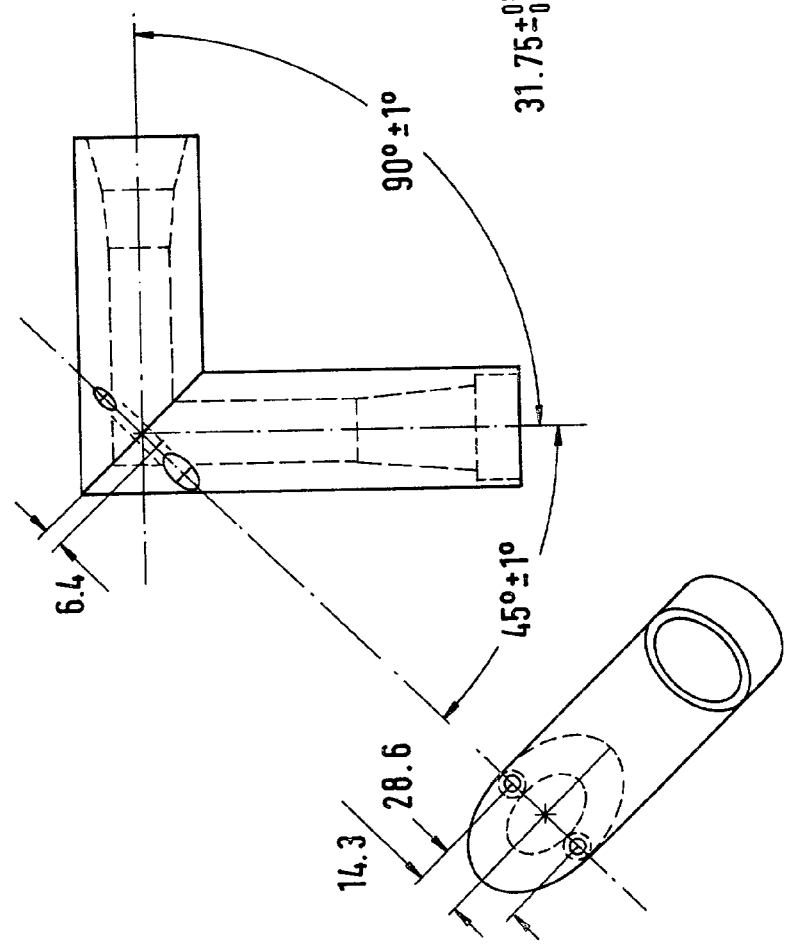
Fig.2b
Fig.2a

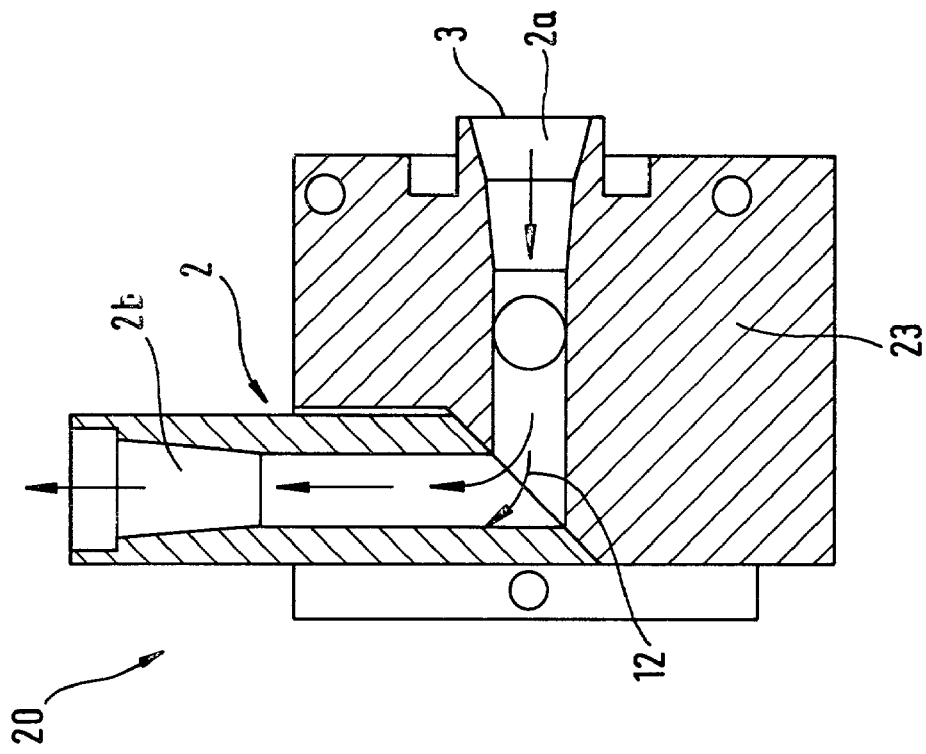
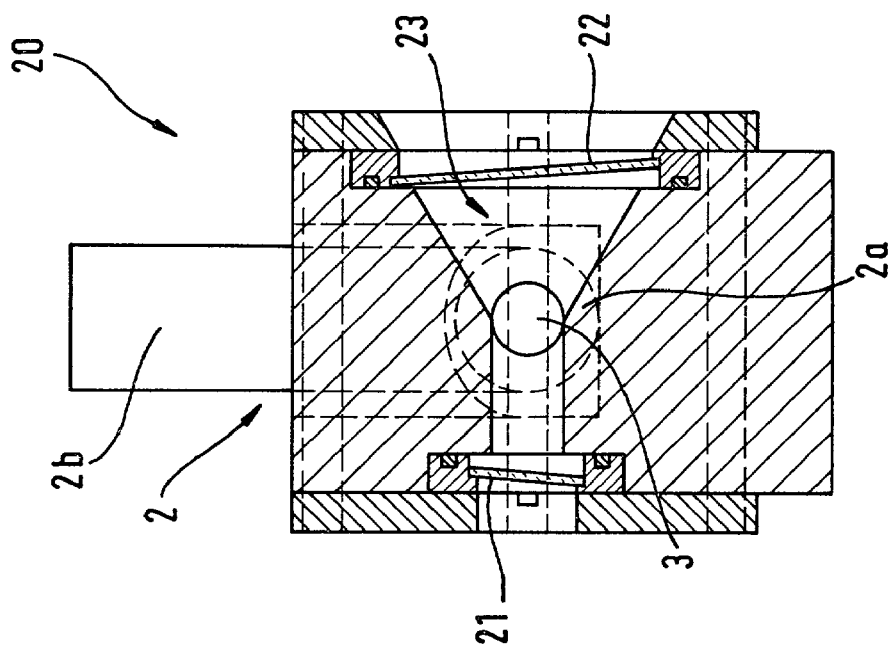

PROCESS FOR DETERMINING THE PARTICLE SIZE DISTRIBUTION OF AN AEROSOL AND APPARATUS FOR CARRYING OUT SUCH A PROCESS

BACKGROUND OF THE INVENTION

The invention relates to processes for determining the size distribution of the particles contained in an aerosol, especially the particles of a pharmaceutical formulation.

The invention also relates to an apparatus for carrying out such a process.

Within the scope of the invention the term "pharmaceutical substance" refers to the active ingredient of a medicament which is usually also known as a drug or active substance.

The term "pharmaceutical formulation" is to be interpreted broadly, to cover formulations in the form of solutions, suspensions and powders, in particular. In a solution formulation the pharmaceutical substance is dissolved in a solvent, whereas in a suspension or powder formulation the pharmaceutical substance is present in solid form. Whereas in a suspension formulation it is mixed with a suspension agent and the pharmaceutical substance is contained in this suspension agent in the form of suspended particles, a powder formulation does not have any solvent or suspension agent in this sense but is present to some extent in pure form, as a pure powder.

A solution formulation is prepared and metered using an atomiser or nebuliser, preferably a nebuliser, in which a quantity of less than 100 ml, preferably less than 50 ml, preferably less than 20 ml of the formulation is prepared.

An apparatus of this kind for propellant-free nebulising of a metered amount of the above-mentioned pharmaceutical formulations is described in detail, for example, in International Patent Application WO 91/14468 "Atomizing Device and Method" and also in WO 97/12687, FIGS. 6a and 6b. In a nebuliser of this kind a pharmaceutical formulation is converted into an aerosol by the use of high pressure, up to 500 bar, the particles introduced having a diameter of less than 100 μm, preferably less than 20 μm.

Apart from this device, other inhalers known from the prior art may also be used in the process according to the invention, such as the MDI (metered dose inhaler) or powder inhalers such as the one known by the trademark Handi-Haler®, for example.

In nebulisers of this kind the formulations are stored in a reservoir and for this reason the formulations used must be sufficiently stable when stored.

It is essential in the pharmaceutical industry to measure the particle size distributions of aerosols in order to assess the characteristics of deposition in the lungs and bronchial region, as will be shown hereinafter.

In a number of applications, particularly in the case of diseases of the lungs and bronchial region, the pharmaceutical substance is provided in the form of an inhalable medicament. The pharmaceutical formulation is atomised to form an aerosol. The aerosol thus produced can then be transported in a carrier medium, e.g. air.

For example, when an asthma spray is used, a pharmaceutical formulation stored in an atomiser is finely atomised through a nozzle, by brief actuation, and introduced into the ambient air breathed in by the patient, this ambient air acting as the carrier medium. The air enriched with the pharmaceutical formulation forms an aerosol, which is inhaled.

Inhalable preparations demand a certain form for the medicament. As a rule, micronised pharmaceuticals or active substances in solid form are used. However, in theory, the drug may be present in liquid or solid form, e.g. as a powder, while solid particles do not dissolve in the solvent in the traditional sense or are present in pure form.

To ensure that the pharmaceutical substance is capable of being inhaled, stringent demands are made of the particle size, particle size distribution, morphology, stability and flow characteristics.

As a rule, not all the inhaled dose of the pharmaceutical substance reaches the lungs but only part of this dose. The amount of the composition which actually enters the lungs is critically influenced by the particle size. For this reason, particles with a diameter of less than 20 μm, preferably less than 5 μm and greater than 0.3 μm are preferred.

The diameter of the particle should fall within the range specified and should additionally have the narrowest possible size distribution. Larger particles are deposited too early, in the upper respiratory tract, when breathed in, whereas smaller particles are not deposited in the lungs and are breathed out again.

For example, when an asthma spray is used, a pharmaceutical formulation stored in an atomiser is finely atomised through a nozzle, by brief actuation, and introduced into the ambient air breathed in by the patient, this ambient air acting as the carrier medium. The air enriched with the pharmaceutical formulation forms an aerosol, which is inhaled.

To ensure that the pharmaceutical substance is capable of being inhaled, stringent demands are made of the particle size, particle size distribution, morphology, stability and flow characteristics.

As a rule, not all the inhaled dose of the pharmaceutical substance reaches the lungs but only part of this dose. The amount of the composition which actually enters the lungs is critically influenced by the particle size. For this reason, particles with a diameter of less than 20 μm, preferably less than 5 μm and greater than 0.3 μm are preferred.

The diameter of the particle should fall within the range specified and should additionally have the narrowest possible size distribution. Larger particles are deposited too early, in the upper respiratory tract, when breathed in, whereas smaller particles are not deposited in the lungs and are breathed out again.

By the particle diameter within the scope of the present invention is meant the aerodynamic particle diameter, which is defined as the equivalent diameter of a sphere with a density of 1 $g/cm^3$ which has the same sedimentation speed in air as the particle under investigation.

Against this background it is easily understandable that the pharmaceutical industry has a need for a process which can be used to determine the particle size distribution of aerosols.

However, the legislators, and particularly the health authorities, also demand accurate knowledge of the dose that is actually administered, i.e. the proportion of the total dose inhaled which is deposited in the lungs and bronchial region.

Moreover, apart from the absolute quantity administered, the size distribution affects the bioavailability of the pharmaceutical substance in that, although the absolute amounts are the same, a large number of small particles have a different bioavailability from a small number of large particles.

According to the prior art, three conventional methods are used to determine the particle size distribution.

A first, widely used method of determining particle size distribution is the so-called impaction method using the Andersen cascade impactor. The cascade impactor is a standardised apparatus for carrying out a standardised measuring process, the so-called impaction method; both the process and the apparatus are described in detail in drugs manuals (cf. also European Pharmacopoeia, $3^{rd}$ Edition, Supplement 2001, 2.9.18 Preparation for inhalation).

FIG. 1 shows the Andersen cascade impactor in diagrammatic side view and partially in section (loc. cit. page 122). The cascade impactor (1) is acted upon by the aerosol which is under investigation through the inlet opening (3) of a right-angled inlet tube (2).

The inlet (2) is a standardised component (loc. cit. page 120) which is also known as a USP throat and simulates the oropharyngeal-cervical cavity in humans. To illustrate the USP throat, FIG. 2.9.17-7 (induction port) is reproduced in FIGS. 2a to 2d.

FIG. 2d shows the USP throat in perspective view, while FIGS. 2a to 2c serve to illustrate the dimensions envisaged. FIGS. 2a to 2d are intended to give an overall impression of the USP throat and show that it is a component with an extremely detailed specification, leaving no leeway for the manufacturer or user.

As with the pharmaceutical formulation administered to the patient with the ambient air breathed in, with which it forms an aerosol, is passed through the oral and pharyngeal cavities into the windpipe and from there is passed into the lungs to the bronchi, in the Andersen cascade impactor (1) as well the aerosol is conveyed along a curved flow path through the non-linear USP throat (2) to the actual sample collector (5).

In accordance with human anatomy, the aerosol flow through the entry opening is conveyed into a first section (2a) of the USP throat (2) and then into a second section (2b) which is connected to the first section (2a) and arranged substantially perpendicular thereto.

The particles of the aerosol are subjected to radially outwardly directed centrifugal forces on account of the nonlinear direction of flow and the resulting curved flow path. If the mass of the aerosol particles exceeds a certain size, these particles can no longer follow the deflected flow but are deposited on the walls of the USP throat (2).

FIG. 1 shows the flight path (12) of a particle which cannot follow the direction of flow and hits or is deposited on the inner wall of the second section (2b) of the USP throat (2).

This is in principle the first stage of the Andersen cascade impactor which simulates the deflection of the aerosol breathed in by the patient in the pharyngeal cavity and the resulting deposition of pharmaceutical formulation in the pharyngeal cavity.

The USP throat (2) is connected to the actual sample collector (5) via a connecting member (4), which is also standardised (loc. cit., page 123). The aerosol flow expands in the connecting member (4) and is guided towards the first stage or cascade ($6_1$) of the cascade impactor (1)

The cascade impactor (1) is a substantially cylindrical container of modular construction through which the aerosol fed in travels from top to bottom, passing through a number of stages, the so-called cascades, while the aerosol particles contained in the carrier medium are deposited in a sequence from coarse to fine or from heavy to light.

Each stage or cascade ($6_1$, $6_2$, $6_3$, $6_4$, $6_5$, $6_6$, $6_7$, $6_8$, $6_9$) comprises a plurality of impactor nozzles ($7_1$, $7_2$, $7_3$, $7_4$, $7_5$, $7_6$, $7_8$). An impactor nozzle (7) of this kind is shown diagrammatically in side view and in section in FIG. 3.

The aerosol which acts on the nozzle (7) is deliberately accelerated in the inlet aperture (8) of the nozzle (7) by a defined constriction of the cross section of the nozzle entrance and then deflected by means of an impactor plate (11). As in the deflection of flow in the USP throat (2), here too the curved path of movement and the centrifugal forces acting on the particles as a result cause particles of a certain mass to be deposited.

FIG. 3 shows the flow lines ($10_1$, $10_2$) of the aerosol flow, which the lighter particles essentially follow without colliding with the impactor plate (11). FIG. 3 also shows the flight path (12) of a particle striking the impactor plate (11) because of its excessively great mass.

The nozzle (7) acts to some extent as a filter for filtering out particles exceeding a given mass from the aerosol flow and depositing them on the impactor plate (11). Because of the fact that it is a standardised apparatus and a standardised process, accurate information is available as to the conditions in the region of the nozzle. For each cascade the precise mass $m_{ab}$ of the particles deposited on the impactor plate (11) here is known.

After passing through the first stage or cascade ($6_1$) and after the first depositing of heavy particles, the aerosol passes through eight more cascades ($6_2$ to $6_9$) as shown in FIG. 1, while the geometry of the impactor nozzles (7) varies or becomes finer from stage to stage and allows finer and finer, i.e. lighter, particles to be filtered out.

The aerosol particles deposited in a certain stage thus have a specific mass which is within a very narrow window bounded by an upper and lower limit.

As the last stage (not shown in FIG. 1) a filter may be provided which collects all the particles that have not previously been deposited and thus, together with the impactor plates (11), makes it possible to determine the absolute total mass of the pharmaceutical formulation fed into the impactor.

After the aerosol has passed through the impactor, the impactor plates (11) of each cascade are removed and subjected to extensive analysis. The main priority is to determine the particle size distribution. Theoretically, first of all the total mass of pharmaceutical formulation impacted or deposited on each impactor plate could be determined. By knowing the mass $m_{ab}$ of the particles deposited in each stage the number of particles deposited in each cascade can be calculated.

In practice however, it has been found that the measurements thus obtained are not reproducible within narrow limits. Tests have shown that some of the pharmaceutical formulation evaporates during the measuring process.

Because of its unsaturated state the carrier medium can absorb additional liquid, and therefore liquid may be, and generally is, given off from the particles to the carrier medium by evaporation.

The evaporation of the particle droplets leads to a change in the particle mass of each individual particle and hence to a reduction in the particle diameter and consequently to a measurement which is falsified by evaporation.

The fact that the effects of evaporation may be significant is demonstrated in FIG. 4, which shows the lifespan of a drop of water depending on the initial droplet diameter for various relative humidities (0%, 50%, 100%) at 20° C. (William C. Hinds "*Aerosol Technology—Properties, Behavior, and Measurement of airborne Particles*", page 270, ISBN 0-471-08726-2).

Small particles have a short lifespan and may evaporate during measurement, so that they are no longer taken into consideration within the scope of the particle size distribution.

For the reasons stated it is not sufficient just to determine the total mass of the pharmaceutical formulation deposited on each impactor plate. Moreover, the pharmaceutical formulation of each impactor plate has to be subjected to analysis to determine the concentrations of the contents. Partial evaporation of the solvent or suspension agent causes concentration of the pharmaceutical substance and the other ingredients of the aerosol droplet.

On the basis of the degree of concentration of the pharmaceutical substance conclusions are drawn as to the fraction of the particle which is evaporated. Taking this evaporated fraction into consideration acts as a corrective when determining the particle size distribution and leads to a different total mass for the pharmaceutical formulation deposited on each impactor plate.

The pharmaceutical formulation deposited on the impactor plates (11) may, for example, be analysed for its composition by the HPLC method.

Further tests have shown that in spite of taking account of the evaporation as described above, the results still vary from one measurement to the next and it is desirable to increase the reproducibility still further. Other tests have shown that simply allowing for the mass of the evaporated fraction of the aerosol particles is not enough.

If a liquid pharmaceutical formulation contains acids or bases to adjust the pH, the evaporation that occurs during measurement leads to a raising or lowering of the pH. Consequently, in pH-sensitive active substances, decompositions occur, with the result that the analysis of the concentration of the active substance in the fractions deposited no longer corresponds to the concentration which was actually present in the original aerosol droplet. This procedure thus comes up against its limitations and can only be used to a limited extent as a corrective for the evaporation effect. A pharmaceutical solution or suspension might, for example, contain an acid X as excipient, in addition to the pharmaceutical substance A and water as the solvent. If some of the solvent water is evaporated, the pH is lowered and the particle becomes increasingly acidic, triggering breakdown of the pharmaceutical substance. The same is true if the pharmaceutical formulation contains a base.

The analysis, i.e. the evaluation of the measurements made with the cascade impactor, is extraordinarily time-consuming and labour-intensive. The entire apparatus is taken to pieces in order to gain access to the multiplicity of impactor plates (11). Each impactor plate is weighed and analysed. Thus, as a rule, only a few measurements can be done per day and there is a considerable time span between the actual measuring and the results of the measurements becoming available.

Another process for determining the particle size distribution of an aerosol, which is far less time-consuming and labour-intensive than the impactor method, is the so-called laser diffraction method. Unlike the impactor method the laser diffraction method does not require any complex analysis and therefore makes it possible to work considerably faster and to obtain the results of the measurements much more quickly.

DIN-ISO 13320-1 (First Edition 1999 Nov. 1) describes laser diffraction processes. In them, parallel light is transmitted perpendicular to an aerosol flow using a laser. The particles contained in the aerosol flow obstruct the laser beams, with the result that the light beams are diffracted on the particles. The scattered light emerging at the opposite side of the incident laser beam, which is generated by the diffraction of the laser beams on the particles, produces a circular interference pattern with concentric rings and is fed to a detector, usually a semiconductor detector. The usual methods of evaluating this interference pattern are Mie scattering and the Fraunhofer method.

Whereas the aerosol flow to be investigated is generally fed continuously to the cascade impactor through a USP throat, the particle size distribution of an aerosol is determined by the laser diffraction method according to the prior art on the free-flowing aerosol, i.e. usually on a one-off, conical, inhomogeneous and therefore non-reproducible metered stream.

However, a disadvantage of the laser diffraction method, as with the impactor method, is the fact that some of the aerosol particles are evaporated and thus the measurements are falsified. Although measurement of the aerosol by the laser diffraction method can be carried out much faster than the impactor method, in which the aerosol flow has to travel along a long flow path, the evaporation effect also plays a part in the laser diffraction method.

Precisely in the case of aerosols in which the particles are in the form of drops of liquid there is a danger of at least partial evaporation of the liquid aerosol particles, which means that the effects described are particularly significant in formulations in the form of solutions and suspensions.

The functional correlation shown in FIG. 4 and the need to take it into account were verified experimentally.

Experiments with the cascade impactor at various relative humidities have shown that measurements of the particle size distribution of an aerosol should most sensibly be carried out at high relative humidities, as the evaporation effect crucially influences the measurements if the humidity of the air is too low and finally high humidity levels also correspond to the actual conditions in the human oropharyngeal-cervical cavity. It should be taken into consideration that the processes described are to be used to determine the characteristics of deposition in the lungs and bronchial region, and for this reason every attempt should be made to simulate the conditions prevailing therein, i.e. pressure, temperature and humidity.

A third method of measuring aerosols is the scattered light method. Such a method is described by Dr.-Ing. H. Umhauer in VDI Berichte 232 (1975), pages 101ff. "*Ermittlung von PartikelgröBenverteilung in Aerosolströmungen hoher Konzentration nit Hilfe der Streulichtmethode*".

This method is suitable for measuring very fine particles with a detection limit which may be well within the submicroscopic range. The measuring process is set up as a counting process which detects the particle size and counts the individual particles so that it is possible to make pronouncements as to both the quality and quantity of the particles.

A disadvantage of the scattered light method is that a small measuring volume has to be defined, e.g. with sides 100:m long, because only one particle may ever stop in the measuring volume if clear scattered signals are to be obtained. The apparatus and the calibration thereof are correspondingly complex. In practice the scattered light method has proved to be inferior to the laser diffraction method as its results are less reliable.

Moreover, the scattered light method, like the laser diffraction method, suffers from the evaporation effect with the associated disadvantages.

As in the conventional laser diffraction process, the scattered light method is also carried out on a free flow of aerosol.

To sum up, it can be said of the prior art that the cascade impactor is highly time-consuming and costly because of its complicated analysis, whereas the scattered light method and also the laser diffraction process, while offering comparatively fast processes, suffer from the evaporation effect, like the cascade impactor.

Against this background the problem of the present invention is to provide a process for determining the particle size distribution of an aerosol which counteracts the disadvantages of the prior art described, and which minimises the influence of the evaporation of the aerosol particles and increases the reproducibility of the measurements.

A further aim of the process according to the invention is to measure liquid pharmaceutical aerosols for their particle sizes which contain an active substance which responds to changes in pH by breaking down.

Another secondary aim of the invention is to provide an apparatus for carrying out such a process.

BRIEF SUMMARY OF THE INVENTION

The present invention provides a process to determine the particle size distribution of an aerosol, especially an aerosol of a pharmaceutical formulation. The process of the present invention comprises the following steps:
  preparing a carrier medium which is saturated with a conditioning agent according to a given degree of saturation,
  mixing the conditioned carrier medium with the pharmaceutical formulation to produce a conditioned aerosol, and
  introducing the conditioned aerosol into at least one measuring cell and measuring the conditioned aerosol in order to determine the particle size distribution of the aerosol.

BRIEF DESCRIPTION OF THE DRAWINGS

FIGS. 2a to 2d show an USP throat with standardised geometric measurements.

FIGS. 6a to 6b show side views of an angled measuring cell.

DETAILED DESCRIPTION OF THE INVENTION

Figure 1:
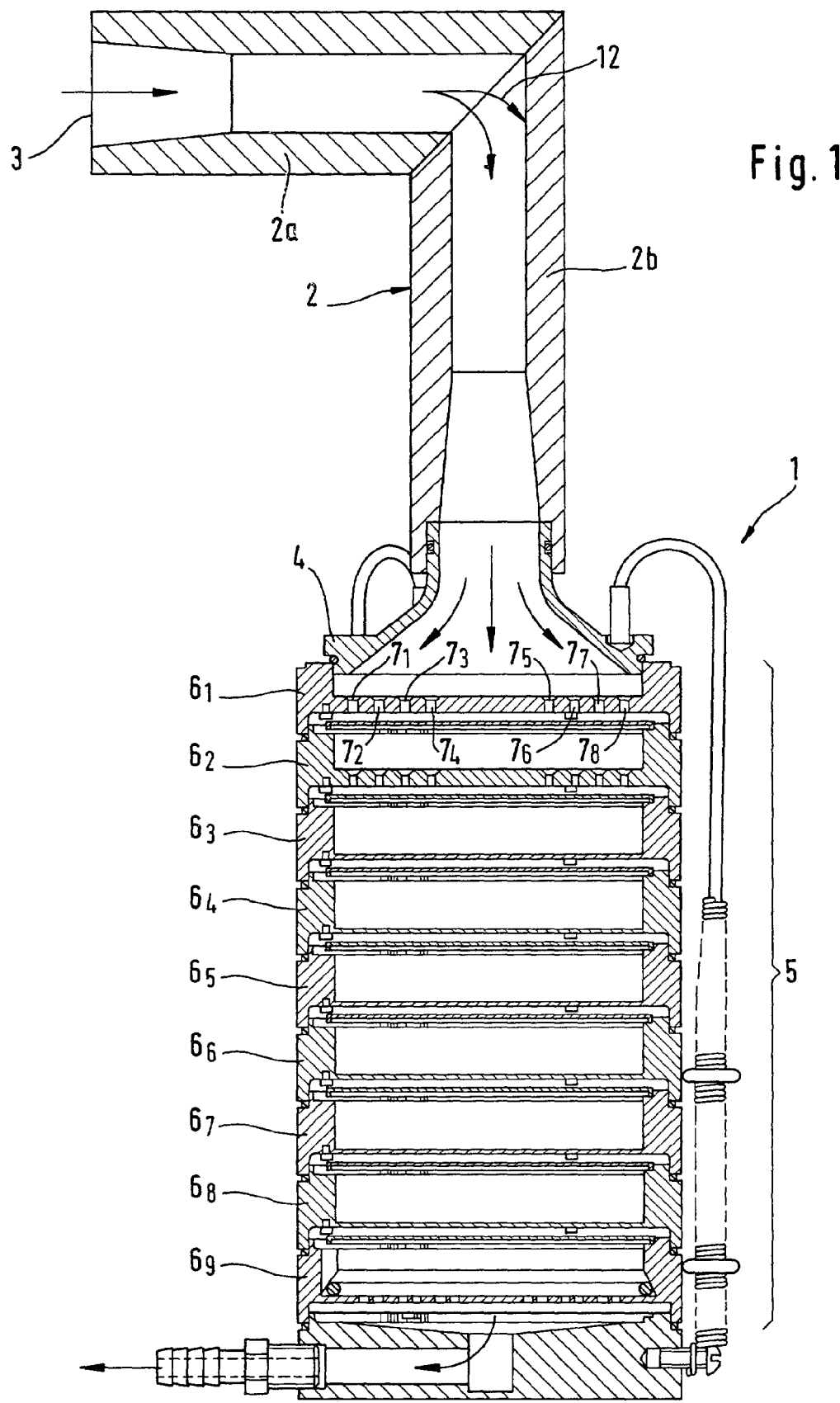
FIG. 1 is a side view of an Anderson impactor with an USP throat.

Using the process according to the invention, the carrier medium into which the aerosol is introduced is enriched with a conditioning agent according to a given degree of saturation. This measure counteracts any evaporation of the particles of a formulation in the form of a solution or suspension and all the other disadvantages connected with evaporation, particularly in substances which are sensitive to changes in pH.

In addition, the enrichment of the carrier medium with a conditioning agent mimics the actual conditions—particularly the high level of humidity—in the human oropharyngeal-cervical cavity, thereby creating measuring conditions which are as realistic as possible. Additionally the temperature and pressure can be adjusted as required.

The conditioning agent thus has two functions, while the establishment of a relative humidity, for basically all pharmaceutical formulations, which corresponds to the actual conditions ensures that the particle size distribution determined for the aerosol is as realistic as possible, thereby increasing the reliability of the measurement for evaluating the deposition characteristics in the lungs and bronchial region.

In the case of solution or suspension formulations the degree of saturation of the carrier medium is preferably more than 80%, more preferably more than 90%, most preferably more than 95%. Ideally it is 100%.

The carrier medium conditioned in this way is mixed with the pharmaceutical formulation under investigation in accordance with the process according to the invention to produce a conditioned aerosol. Atomisers or nebulisers as described in the introduction to the specification may be used for this purpose in the case of pharmaceutical solutions, for example.

Advantageously, once again an attempt is made to simulate reality as accurately as possible, for which reason the atomiser is preferably arranged in a mixing chamber in which the aerosol produced by the atomiser is mixed with the carrier material (air or some other gas) in order to direct the mixture in a defined flow from there through the measuring device. One advantage of the aerosol being guided in this way is that this approximates very closely to the conditions that prevail when an aerosol is being breathed in by a patient.

On the other hand, the carrier flow avoids any impact on the window of the measuring cell(s) in the case of liquid aerosols, which is an advantage particularly in the laser diffraction method. To produce this effect it is not necessary for the carrier material to be conditioned, i.e. saturated with water.

The carrier material may, for example, flow through slots in the mouthpiece of the inhaler into the interior of the mouthpiece, where it is mixed with the cloud of aerosol produced by the inhaler and introduced therein.

The conditioned aerosol thus generated is then fed into at least one measuring cell and measured in order to determine the particle size distribution of the aerosol.

In an advantageous process, the measurement of the conditioned aerosol is carried out by the laser diffraction method. The laser diffraction method is a fast method which gives rapid access to the measurements.

In an advantageous process, the measurement of the conditioned aerosol is carried out by the scattered light method. The scattered light method gives not only a qualitative result—the particle size—but also a quantitative result, as the particles are not only measured for their size but are also counted.

In an advantageous process the measurement of the conditioned aerosol is carried out by the impactor method. As the impactor method is the one which is most widespread—inter alia because it is recommended and accurately described in the pharmacopoeias—and has been used for a great many measurements, this process offers a large fund of comparative measurements. Thus, when new pharmaceutical formulations and/or new metering devices, particularly atomisers, are being tested it may be sensible to compare them with conventional pharmaceutical formulations or metering devices.

In an advantageous process the measurement of the conditioned aerosol is carried out by the laser diffraction process and the scattered light method. Using the two methods together combines the advantages of both methods, namely the accuracy of the laser diffraction process in qualitative terms with the scattered light method as a particle counting method and hence the possibility of making quantitative pronouncements.

Favourable methods are characterised in that the conditioned aerosol is also measured by the impactor method. In this alternative embodiment of the process the impactor method additionally used serves primarily to verify the measurements obtained by the process according to the invention. Tests have shown that the measurements obtained with the two methods largely agree.

In the process according to the invention, the particle size distribution of the aerosol may optionally be carried out either by the laser diffraction method or by the scattered light method or using both methods, i.e. the laser diffraction method and the scattered light method, while if both methods are used they are carried out together in one measuring cell or a separate measuring cell is provided for each process, so that both processes have their own measuring cell to suit their own particular requirements.

Experimental tests have shown that the process according to the invention, particularly the laser diffraction method, in a conditioned aerosol flow agrees closely with the measurements obtained using the Andersen cascade impactor.

In an advantageous embodiment of the process in which a solution formulation, i.e. a solution of pharmaceutical substance, is used, the solvent in which the pharmaceutical substance is dissolved is used as the conditioning agent. In order to prevent evaporation of the solvent contained in the aerosol particles, the solvent whose evaporation is to be inhibited is advantageously added to the carrier medium as a conditioning agent. The addition of the solvent as a conditioning agent lowers the vapour pressure of the solvent in the carrier medium, thereby making it more difficult for the liquid aerosol particles to evaporate, or reducing the amount of evaporation.

In preferred variants of the process in which a suspension formulation, i.e. a suspension of pharmaceutical substance, is used, the suspension agent containing the pharmaceutical substance in the form of suspended particles is used as the conditioning agent. The reasons for this are similar to those mentioned for the solution formulation. In order to prevent or reduce the evaporation of the suspension agent contained in the aerosol particles, the suspension agent is preferably added as the conditioning agent to the carrier medium, as a result of which the vapour pressure of the suspension agent in the carrier medium is lowered and hence the tendency to evaporation is counteracted.

According to favourable variants, if a propellant-free dissolved or suspended formulation is used, the solvent or suspension agent is used as the conditioning agent. Water, water/alcohol mixtures or alcohol are preferred. The preferred alcohol is ethanol. Water is most preferred.

Because the powder formulation, unlike the solution and suspension formulations, does not have any solvent or suspension agent, water is preferably added as conditioning agent to the carrier medium.

This comes very close to the actual conditions because the moist air breathed in by the user, which acts as a carrier medium for the powder, can be satisfactorily simulated or reproduced experimentally by air saturated with water as conditioning agent.

In contrast to the other two pharmaceutical formulations, in a powder formulation a preferred process is one wherein the carrier medium does not exceed a saturation level of 75%, as the pharmaceutical substance present in the form of a fine powder tends to form larger particles and particularly to cake together at higher saturation levels.

Also advantageous are variants of the process in which air is used as the carrier medium. One reason for this is that again the use of air as a carrier medium corresponds to the actual conditions and thus provides a good simulation in the experiment.

In advantageous processes a USP throat, through which the aerosol flow passes, is used within the scope of the measurement. This simulates the flow through the oropharyngeal-cervical cavity.

In advantageous processes the measurement of the particle size distribution of the aerosol by the laser diffraction process and/or the scattered light method is carried out in at least one measuring cell which is separated from the surrounding atmosphere. To maintain the conditioning and stabilise the conditioned aerosol, i.e. to separate it from the surrounding atmosphere, a suitable prepared measuring cell is advisable.

Preferred embodiments of the process are those wherein the measurement of the particle size distribution of the aerosol by the laser diffraction method and/or the scattered light method is carried out in at least one measuring cell integrated in the USP throat. The USP throat is a test device recognised by the FDA (Food and Drug Agency).

The or each measuring cell may be arranged both in the first section of the USP throat and also in the second section of the USP throat. Moreover, when two measuring cells are provided, there is the possibility of arranging one measuring cell in the first section and the second measuring cell in the second section of the USP throat, while once again it is also possible to arrange both measuring cells in the first or second section of the USP throat.

This or each measuring cell is in fact shown in FIGS. 2a to 2d and integrated in the USP throat described in detail hereinbefore.

It is thus possible to carry out the laser diffraction process and/or the scattered light method on a defined, well known aerosol flow. The measurement of the particle size distribution on a free, inhomogeneous and non-reproducible aerosol cloud, which is regarded as disadvantageous, is thus replaced by a defined process using standardised equipment.

Surprisingly, tests have shown that by suitably modifying the USP throat in order to integrate at least one measuring cell the advantages of the laser diffraction process and/or the scattered light method can be combined with the advantages of the impactor method using the USP throat, while the experts will be astounded to discover that the modification, i.e. the structural alteration of the USP throat, has no effect on the measurements obtained for the particle size distribution.

Figure 5:
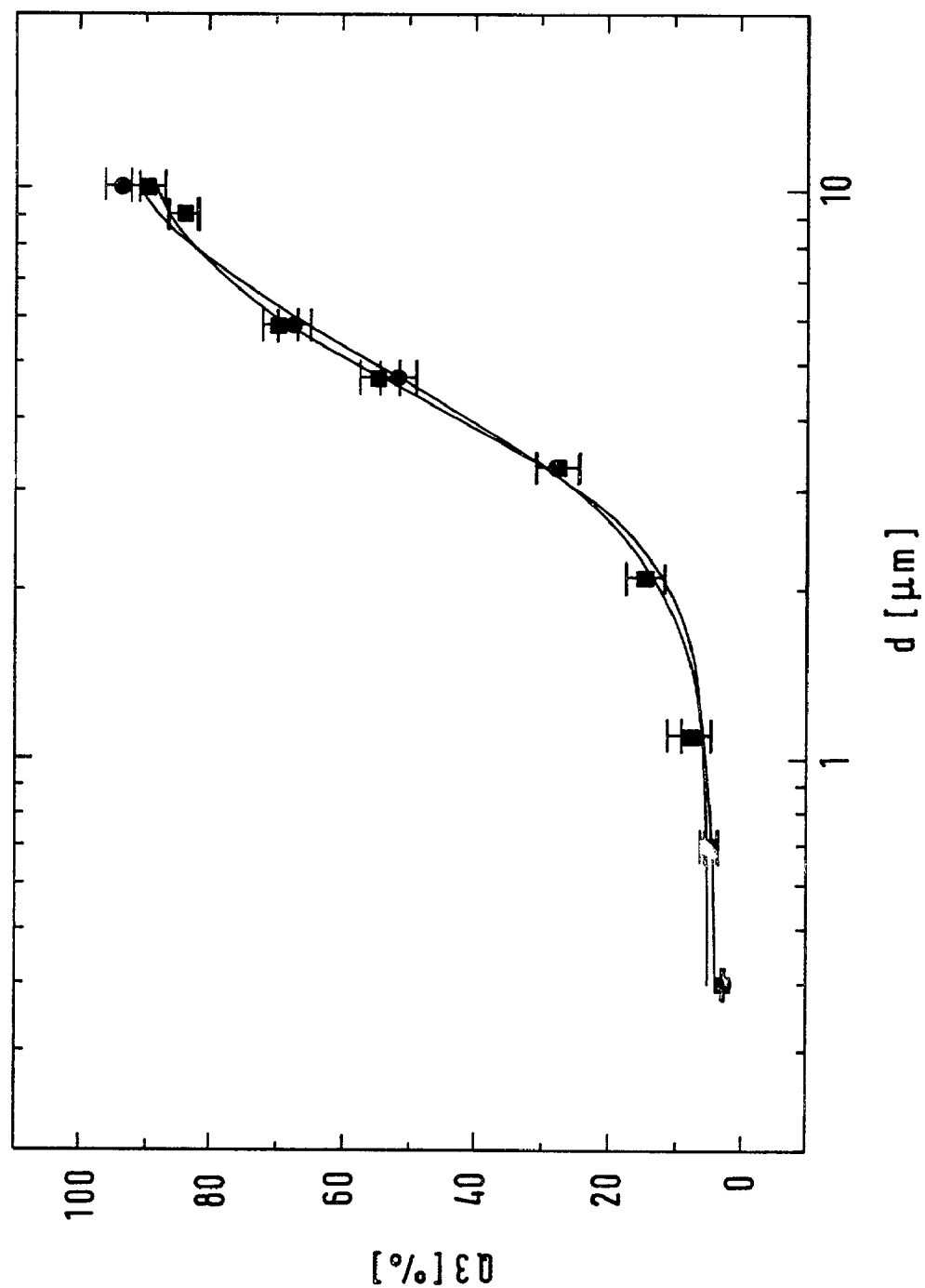
FIG. 5 is a chart comparing properties of a conventional USP throat with one modified with an angled measuring cell according to the present invention.

This has been verified in numerous experiments, in which a conventional cascade impactor was fitted with the modified USP throat and comparative measurements were taken which were compared with the measurements using the conventional USP throat. The results of the comparative measurements are shown in FIG. 5, in which the distribution sum $Q_3$ is shown as a function of the particle diameter. The measurements marked with a small square represent the results of a cascade impactor fitted with an original throat, whereas the measurements marked with a small circle are the measurements obtained with a cascade impactor fitted with the modified USP throat according to the invention. Very good correspondence is obtained, so that it may reasonably be concluded that the modification of the USP throat does not substantially alter the data obtained with the original throat.

Thus, the process according to the invention which provides for the arrangement of at least one measuring cell in the USP throat is suitable for replacing the conventional process using cascade impactors, which do not produce rapid measurements on account of the complicated analysis required.

An advantage of this variant of the process is that the USP throat is an exactly standardised component which simulates the oropharyngeal-cervical cavity in humans, and ensures a precisely defined flow of aerosol.

According to favourable embodiments of the process, the metered aerosol is fed into a separator in order to separate off the particles. This is done in order to determine the total absolute particle mass of the particles or pharmaceutical formulation delivered with the aerosol. A filter may be used as the separator.

This is particularly favourable in conjunction with the variant of the process according to the invention in which the laser diffraction process is not carried out together with the scattered light method but is used on its own. In this case, in fact, there is a need for an apparatus which will provide quantitative information on the particle mass delivered.

Whereas the scattered light method provides both qualitative and quantitative results, i.e. gives information on both the size distribution and on the particle masses, the laser diffraction process can only provide information as to the size distribution and not on the quantity of aerosol particles.

Processes wherein a laser is used as the light source for the laser diffraction process or the scattered light method are favourable. An advantage of the use of a laser is that it emits parallel light.

The problem of the equipment required is solved by an apparatus having:
  a conditioning device for saturating a carrier medium with a conditioning agent according to a given saturation level,
  a metering device for metering and preparing a pharmaceutical formulation,
  a mixing chamber for mixing the prepared, conditioned carrier medium and the prepared pharmaceutical formulation to produce a conditioned aerosol, and
  at least one measuring cell into which the conditioned aerosol is introduced in order to carry out a measurement of the particle size distribution of the aerosol.

In advantageous embodiments of the apparatus, the or each measuring cell for carrying out the impactor method is an impactor, preferably an Anderson cascade impactor.

In advantageous embodiments of the apparatus, the or each measuring cell for carrying out the laser diffraction process has an least one entry window for the entry of a light beam from a light source and at least one exit window for the exit of the scattered light from the light beam, while preferably the or each entry window is arranged at a tilted angle to the incident light beams from the light source and preferably the or each exit window is arranged at a tilted angle to the incident light beams. Reflections are avoided by the fact that the light beam does not strike perpendicularly on the entry or exit window.

According to advantageous embodiments of the apparatus, the or each entry window and the or each exit window are arranged to be tilted at identical—but opposite—angles relative to the incident light beams. As a result of the two windows being tilted opposite ways and at the same angle the offset of the incident and emergent light beams is cancelled out again because of the tilt.

In favourable embodiments of the invention, the or each entry window and/or the or each exit window are constructed to be removable. This makes it possible to clean not only the measuring cell but also the window itself after the measurement has been done and to investigate any deposit of aerosol particles in the measuring cell and on the windows.

According to advantageous embodiments of the invention, the or each entry window and the or each exit window are thin in construction, particularly less than 2 mm thick. An advantage of this embodiment is that the incident or emergent light beam which preferably falls diagonally on the tilted windows and which is diffracted as it enters the glass from the ambient atmosphere undergoes only a small displacement of the beam if the windows are thin.

According to advantageous embodiments of the invention, the or each measuring cell for carrying out the scattered light method has at least one entry window for the entry of a light beam from a light source and at least one exit window for the exit of the scattered light from the light beam, the two windows preferably being arranged substantially at right angles to each other.

The problem of the equipment according to the invention is solved by an apparatus, particularly an apparatus for carrying out the second process according to the invention, which specifically has the following components:
  a metering device for metering and preparing a pharmaceutical formulation,
  a mixing chamber for mixing a prepared carrier medium and the prepared pharmaceutical formulation to produce an aerosol, and
  at least one measuring cell into which the aerosol is introduced in order to measure the particle size distribution of the aerosol by the laser diffraction process and/or the scattered light method, the or each measuring cell being integrated in the USP throat and forming, together with this throat, an angled measuring cell.

The invention also discloses an angled measuring cell, particularly as a component or replacement part for an apparatus for carrying out the process according to the invention, which comprises the USP throat and at least one measuring cell integrated in the USP throat.

According to advantageous embodiments of the measuring cell, the or each measuring cell for carrying out the laser diffraction process has at least one entry window for the entry of a light beam from a light source and at least one exit window for the exit of the scattered light from the light beam.

According to favourable embodiments of the angled measuring cell, the or each entry window is arranged at a tilted angle to the incident light beams from the light source and preferably the or each exit window is arranged at a tilted angle to the incident light beams, while the or each entry window and the or each exit window are arranged to be tilted at identical—but opposite—angles relative to the incident light beams.

In favourable embodiments of the angle measuring cell, the or each entry window and/or the or each exit window are constructed to be removable.

According to advantageous embodiments of the angled measuring cell, the or each entry window and the or each exit window are thin in construction, particularly less than 2 mm thick, the or each entry window and the or each exit window being arranged opposite each other.

According to advantageous embodiments of the angled measuring cell, the or each entry window and the or each exit window of the or each measuring cell for carrying out the scattered light method are arranged substantially at right angles to each other.

Figure 3:
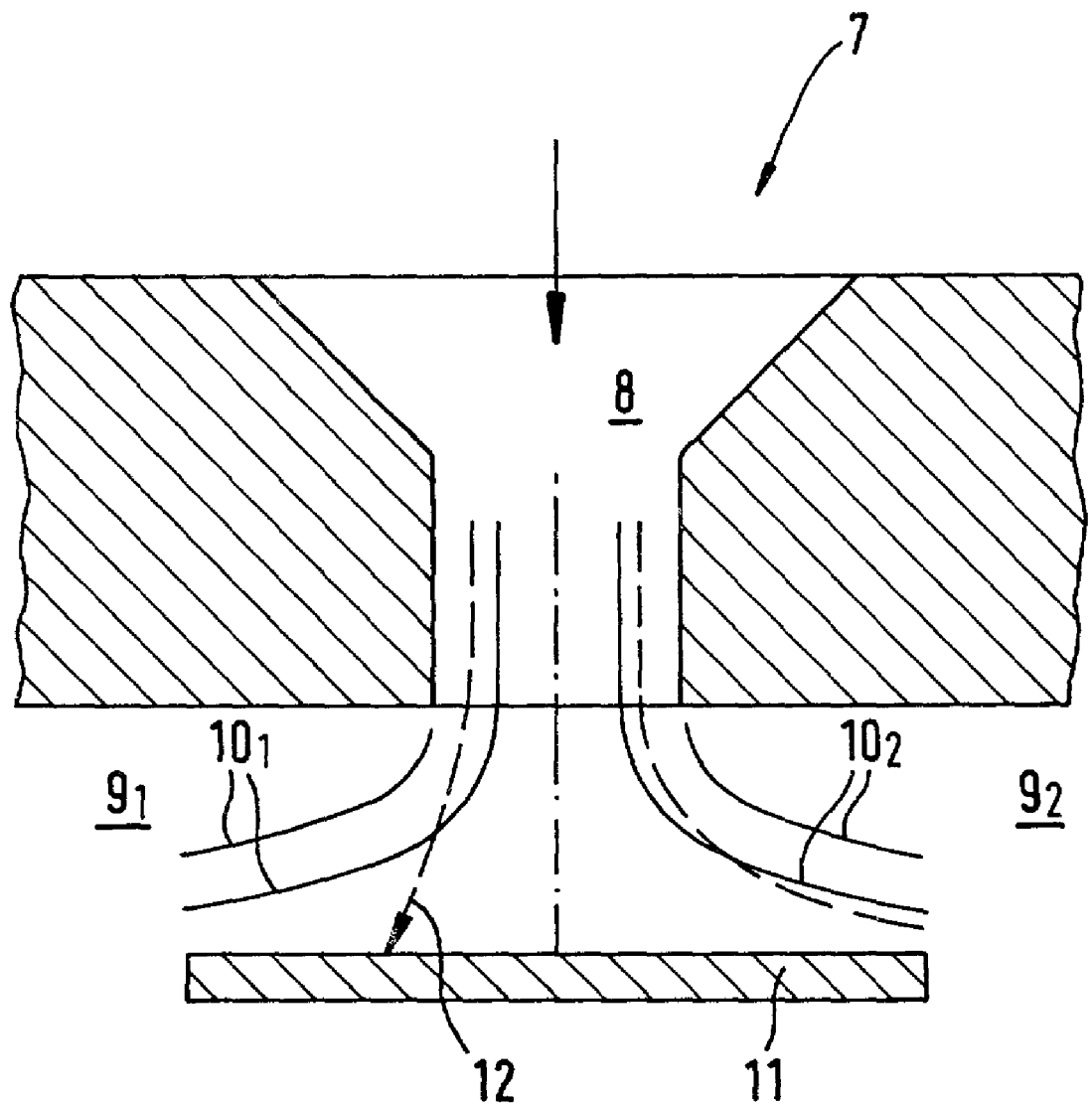
FIG. 3 shows an impactor nozzle.
Figure 4:
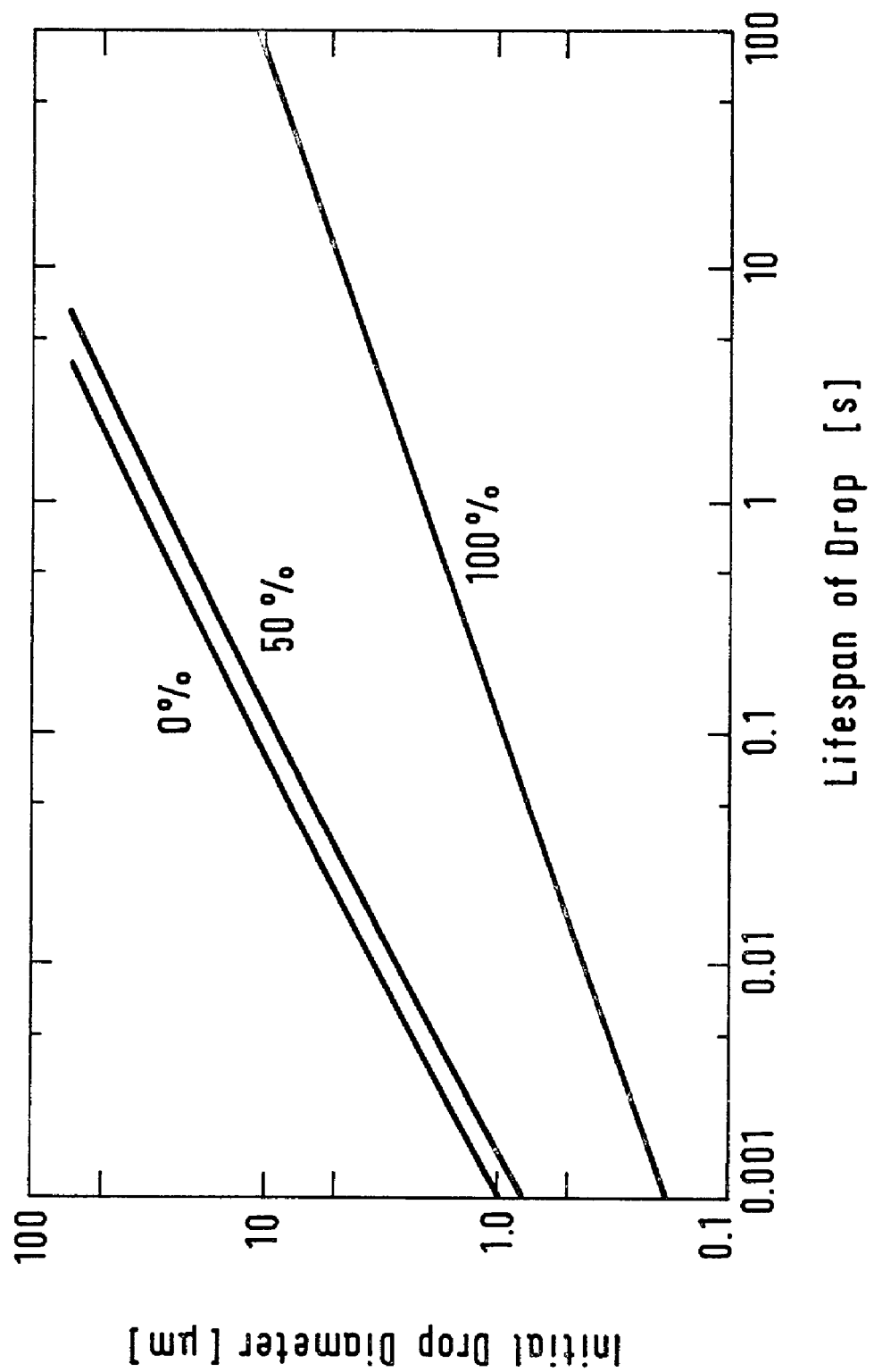
FIG. 4 is a chart showing dependency of droplet size on lifespan of droplet for three(3) different degrees of saturation with water.

The present invention is hereinafter described by reference to an embodiment by way of example illustrated in FIGS. 6a, 6b and 7. Specifically, as noted previously, FIG. 1: shows an Andersen cascade impactor with the USP throat in side view, partly in section, FIGS. 2a to 2d: show the USP throat with its standardised geometric measurements, FIG. 3: shows an impactor nozzle shown diagrammatically and in section in side view, FIG. 4: shows a diagram relating to the dependency of the droplet size on the life of the droplet, for three different degrees of saturation with water, FIG. 5: shows a diagram comparing the properties of a conventional USP throat with those of the angled measuring cell, FIGS. 6a to 6b: show an embodiment of an angled measuring cell in different side views, partly in section, and FIG. 7: shows an embodiment of the apparatus for measuring the particle size distribution of the aerosol.

In FIGS. 1, 2a-2d, 3, 6a-6b and 7, the following numbers are used for the following parts:
1 Andersen cascade impactor
2 throat
2a first section
2b second section
3 entry opening
4 connecting member
5 sample collector
$6_1$ cascade
$6_2$ cascade
$6_3$ cascade
$6_4$ cascade
$6_5$ cascade
$6_6$ cascade
$6_7$ cascade
$6_8$ cascade
$6_9$ cascade
$7_1$ impactor nozzles
$7_2$ impactor nozzles
$7_3$ impactor nozzles
$7_4$ impactor nozzles
$7_5$ impactor nozzles
$7_6$ impactor nozzles
$7_7$ impactor nozzles
$7_8$ impactor nozzles
8 entry opening
$9_1$ exit opening
$9_2$ exit opening
$10_1$ flow lines
$10_2$ flow lines
11 impactor plate
12 flight path of a striking particle
20 angled measuring cell
21 entry window
22 exit window
23 measuring cell
24 conditioning device
25 mixing chamber
26 metering device, nebuliser
27 laser
28 lens
29 semiconductor detector FIG. 6a shows a first embodiment of an angled measuring cell 20 which comprises a USP throat 2 and a measuring cell 23 for carrying out the laser diffraction process. The measuring cell is arranged in the first section 2a of the USP throat, so that the current of aerosol is measured even before the first particle fraction has been deposited in the angled section at the transition from the first section 2a to the second section 2b.

The measuring cell 23, shown in section, has an entry window 21 and an exit window 22. The two windows 21, 22 are constructed to be removable so that after the measurement has been done the measuring cell 23 can be cleaned and examined. Both the entry window 21 and the exit window 22 are tilted slightly, relative to the incident light beam, thus preventing reflection of the incident light beam. The two windows 21, 22 are tilted at the same angle, but opposite one another, in order to compensate for the offset of the beam of the incident laser light as a result of the tilt.

It is clearly apparent that the entry window 21 is relatively small compared with the exit window 22. The reason for this is that the incident light coming through the entry window 21 is an undisturbed beam of light which is propagated in linear manner, whereas the light leaving through the exit window 22 is the scattered light from the incident light beam diffracted on the aerosol particles, for which reason the exit window 22 should also be constructed so that scattered light from a large enough angular area can be accommodated, i.e. is able to leave the measuring cell 23 and be picked up by a detector.

FIG. 6b shows the angled measuring cell 20 shown in FIG. 6a, in a view turned through 90° relative to the position shown in FIG. 6a, partly in section.

It clearly shows the USP throat 2 consisting of the first section 2a and the second section 2b, and the measuring cell 23 integrated therein in the first section 2a. In this way the aerosol flow entering through the inlet opening 3 is measured before it is deflected through the angled section into the second section 2b. The Figure also shows the flight path of a particle striking the inner wall of the second section 2b which with the other particles arriving at this point forms the first deposited fraction of the aerosol flow.

Figure 7:
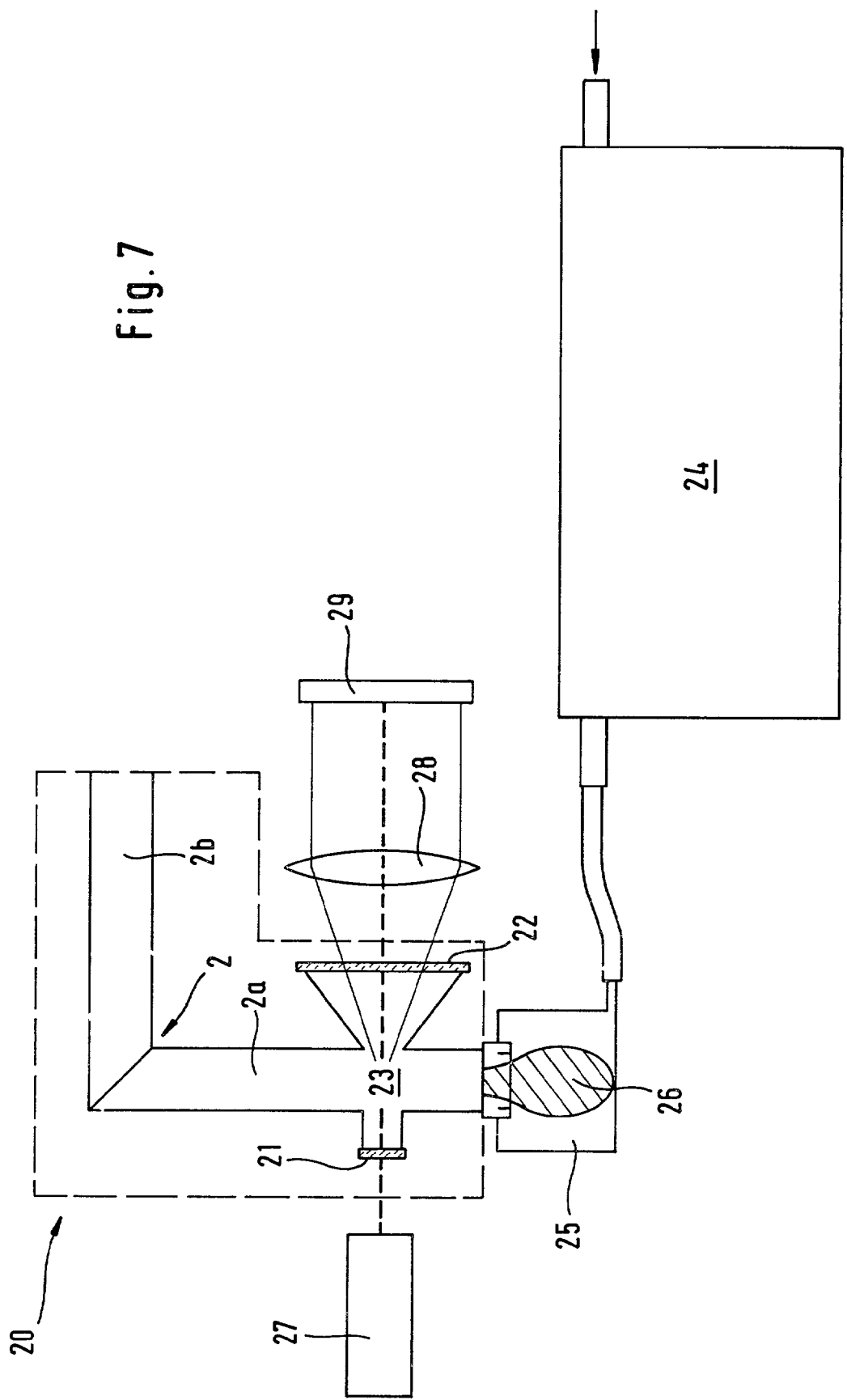
FIG. 7 shows an apparatus for measuring the particle size distribution of an aerosol according to the present invention.

FIG. 7 shows an embodiment of an apparatus for measuring the particle size distribution of an aerosol, shown diagrammatically.

The apparatus comprises a conditioning device 24 for saturating a carrier medium with a conditioning agent to a given degree of saturation. The carrier medium thus conditioned is fed into a mixing chamber 25 which contains a nebuliser to be examined, which atomises a solution of pharmaceutical substance stored therein. The nebuliser 26 acts as a metering device 26 for metering and preparing a pharmaceutical solution. The pharmaceutical solution prepared using the metering device is mixed with the conditioned carrier medium in the mixing chamber 25 to form a conditioned aerosol.

The aerosol conditioned in this way is introduced into a measuring cell 23.

This measuring cell 23 is arranged in a first section 2a of the USP throat 2 and together with the throat 2 forms an angled measuring cell 20, which is surrounded by a dotted line in FIG. 7.

The light emitted by the laser 27 falls through the entry window 21 into the interior of the measuring cell 23 and from there strikes the aerosol flow guided by the first section 2a of the USP throat 2. The incident laser light is diffracted on the particles of the aerosol, which constitutes an obstacle to the light. The scattered light which is generated by the diffraction of the incident laser light on the particles of the aerosol leaves the measuring cell 23 through the exit window 22, is then focussed through a lens 28 and fed into a semiconductor detector 29 for evaluation. After being measured in the measuring cell the aerosol flow is diverted into the second section 2b of the USP throat 2. After passing through the throat 2 or the angled measuring cell 20 the aerosol flow measured by the laser diffraction process can be fed into a particle separator in order to obtain quantitative information on the particle mass; the particle separator may take the form of a filter.

An additional measuring cell for obtaining a measurement by the scattered light method could be provided, in which case this measuring cell would be arranged both in the first section 2a and in the second section 2b of the USP throat 2. This would also make it possible to obtain quantitative information on the particle mass.

The apparatus shown in FIG. 7 could also have an Andersen cascade impactor adjacent to it, which could be used inter alia to verify the particle size distribution of the aerosol determined by the laser diffraction method.

On the basis of the foregoing, the present invention can be summarised as follows:

The measurement of the particle size distribution of an aerosol is of crucial importance in the pharmaceutical industry. The prerequisite for this is a valid method, e.g. the cascade impactor method described in the pharmacopoeias. It requires measurement of the active substance concentration in order to determine the particle size distribution.

However, the above method and other methods as well rapidly lead to an increase or decrease in the pH, which may lead to decomposition of sensitive active substances. Consequently, the particle sizes can no longer be determined precisely, as it is usual to determine the concentration of active substance in order to obtain the particle size.

Surprisingly, it has been shown that by adjusting the relative humidity to 80 to 100%, preferably 90 to 100%, using the solvent on which the solution or suspension formulation is based, preferably water or a water/alcohol mixture (ethanol), the breakdown of the active substance during the measuring process can be totally prevented.

Another advantage of the process according to the invention is that the particle size can be determined irrespective of the nature of the aqueous formulation, i.e. different salt concentrations in the solution or suspension have no effect on the measurement of the particle size.

It has also advantageously been found that the measurement of the particles is not disrupted when water condenses out in the measuring apparatus, particularly the cascade impactor, during the measurement.

Compared with the standard measurement without conditioning the air with a solvent such as water the relative standard deviation can be improved from 10-15% to about 2% using the process according to the invention.

At a relative humidity of 100% the method shows a significantly lower scattering in the MMAD (mass median aerodynamic diameter) than the standard method without conditioning of the air with a solvent such as water.

For the process according to the invention, water saturated with moisture can be produced by passing compressed air through a water bath heated to above ambient temperature; the water temperature is preferably about 30 to 45° C.

The process is preferably used to measure the spray pattern of a propellant-free "soft mist inhaler", preferably known under the trademark Respimat®, disclosed for example in WO 97/12687. Preferred formulations are described in WO 97/01329 and WO 98/27959, to which reference is hereby expressly made.

What is claimed is:

1. An apparatus for determining the size distribution of particles contained in an aerosol of a pharmaceutical formulation, comprising:
    a conditioning device (24) for saturating a carrier medium with a conditioning agent according to a given saturation level to produce a conditioned carrier medium,
    a metering device (26) for metering a pharmaceutical formulation,
    a mixing chamber (25) for mixing the conditioned carrier medium and the metered pharmaceutical formulation to produce a conditioned aerosol of pharmaceutical formulation, and
    at least one measuring cell (23) into which the conditioned aerosol of pharmaceutical formulation is introduced in order to carry out a measurement of the particle size distribution of the aerosol.

2. The apparatus according to claim 1, characterised in the measuring cell is an impactor.

3. The apparatus according to claim 2, characterised in that the impactor is an cascade impactor.

4. The apparatus according to claim 1 characterised in that the measuring cell has at least one entry window (21) for the entry of a light beam from a light source and at least one exit window (22) for the exit of the scattered light from the light beam.

5. The apparatus according to claim 4, characterised in that the entry window (21) is tilted relative to the incident light beam from the light source.

6. The apparatus according to claim 4, characterised in that the exit window (22) is tilted relative to the emergent light beam.

7. The apparatus according to claim 4, characterised in that the entry window (21) and the exit window (22) are tilted at identical—but opposite—angles relative to the incident light beam.

8. The apparatus according to claim 4, characterised in that the entry window (21) and the exit window (22) are constructed to be removable.

9. The apparatus according to claim 4, characterised in that the entry window (21) and the exit window (22) are less than about 2 mm thick.

10. The apparatus according to claim 4, characterised in that the entry window (21) and the exit window (22) are arranged opposite one another.

11. The apparatus according to claim 4, characterised in that the exit window and the entry window of the measuring cell are arranged substantially at right angles to one another.

* * * * *